United States Patent [19]

Fiedler et al.

[11] Patent Number: 4,978,771

[45] Date of Patent: Dec. 18, 1990

[54] PROCESS FOR THE SELECTIVE HYDROGENATION OF UNSATUATED COMPOUNDS

[75] Inventors: Paul Fiedler, Cologne; Hartmuth Buding, Dormagen; Rudolf Braden, Odenthal, all of Fed. Rep. of Germany

[73] Assignee: Bayer Aktiengesellschaft, Leverkusen, Fed. Rep. of Germany

[21] Appl. No.: 195,513

[22] Filed: May 18, 1988

Related U.S. Application Data

[63] Continuation of Ser. No. 928,196, Nov. 7, 1986, abandoned.

[30] Foreign Application Priority Data

Nov. 19, 1985 [DE] Fed. Rep. of Germany ....... 3540918

[51] Int. Cl.$^5$ ................. C07C 255/05; C07C 255/09; C07C 255/13; C07C 255/22
[52] U.S. Cl. ................ 558/459; 525/329.3; 525/331.9; 525/338; 525/339; 546/264; 558/409; 558/442; 558/447; 558/467
[58] Field of Search ............... 558/459, 467; 525/339, 525/329.3, 331.9, 338

[56] References Cited

U.S. PATENT DOCUMENTS

| | | | |
|---|---|---|---|
| 3,454,644 | 7/1969 | Dewhirst | 568/814 X |
| 3,458,547 | 7/1969 | Coffey | 558/467 X |
| 3,480,659 | 11/1969 | Dewhirst | 558/467 |
| 3,489,786 | 1/1970 | Dewhirst | 558/467 |
| 3,574,716 | 4/1971 | Coffey | 558/467 X |
| 3,700,633 | 10/1972 | Wald et al. | 525/339 |
| 3,700,637 | 10/1972 | Finch, Jr. | 525/339 X |
| 3,700,748 | 10/1972 | Winkler | 525/339 X |
| 3,994,868 | 11/1976 | Inomata et al. | 526/13 |
| 4,631,315 | 12/1986 | Buding et al. | 525/338 |
| 4,673,757 | 6/1987 | Fiedler et al. | 558/459 X |
| 4,746,707 | 5/1988 | Fiedler et al. | 525/338 |
| 4,795,788 | 1/1989 | Himmler et al. | 525/338 |
| 4,812,528 | 3/1989 | Rempel et al. | 525/338 |
| 4,816,525 | 3/1989 | Rempel et al. | 525/338 |

FOREIGN PATENT DOCUMENTS 1138601 1/1969 United Kingdom .
1558491 1/1980 United Kingdom .

OTHER PUBLICATIONS

Linn and Halpern, "Roles of Neutral and Anionic Ruthenium Polyhydrides in the Catalytic Hydrogenation of Ketones and Arenes", *J.Am. Chem. Soc.*, vol. 109, pp. 2969–2974 (1987).
Houben-Weyl, vol. IV, 1c, pp. 57 to 60 and 168 (1980) and a translation thereof of a portion of p. 168.
M. Freifelder, Practical Catalytic Hydrogenation, Wiley Interscience, New York, 1971, pp. 157/158.
J. Chem. Soc., Dalton 1973, pp. 846–854.

*Primary Examiner*—Joseph Paul Brust
*Attorney, Agent, or Firm*—Connolly and Hutz

[57] ABSTRACT

The selective hydrogenation of unsaturated compounds which carry reducible groups containing nitrogen succeeds in a homogeneous phase with the preservation of the reducible groups containing nitrogen, characterized in that a compound of the formula

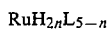

$$RuH_{2n}L_{5-n}$$

is used as a catalyst, in which
L signifies a phosphane or arsane and
n signifies 1 or 2.

3 Claims, No Drawings

PROCESS FOR THE SELECTIVE HYDROGENATION OF UNSATUATED COMPOUNDS

This is a continuation of application Ser. No. 928,196 filed Nov. 7, 1986, abandoned.

The invention concerns a process for the selective hydrogenation of unsaturated, optionally high-molecular compounds which carry reducible groups containing nitrogen.

It is known that C—C-double bonds can be hydrogenated selectively on solid catalysts in presence of reducible groups containing nitrogen. For this purpose palladium or platinum catalysts are used. Yields of up to 90% are achieved by this means (Houben-Weyl, Methoden der Organischen Chemie, Volume IV, 1c, Reduction I (1980), page 168). The selectivity is, however, frequently unsatisfactory. Thus in using platinum oxide for the hydrogenation of 1-cyano cyclohexene only 31% of the desired cyano cyclohexane is obtained (cf. M. Freifelder, Practical Catalytic Hydrogenation, (1971), page 157).

A method of hydrogenating unsaturated nitriles using rhodium complexes as homogeneous catalysts (Wilkinson-complex) is also known. The cyano group is not hydrogenated in this process. As a result of ligand exchange, however, the catalyst can be deactivated with nitriles (cf. Houben-Weyl, loc. cit., pages 57 to 60).

As rhodium complexes of the formula $[(C_6H_5)_3P]_3Rh^IX$ are also suitable for the hydrogenation of nitriles (DE-AS 1 793 616), it can be expected that the selectivity is not always adequate for the hydrogenation of olefinic double bonds in presence of nitrile groups.

It is known from U.S. Pat. No. 3,454,644 that it is possible to hydrogenate keto-, formyl-, nitrile-, nonaromatic —C=C and —C≡C-groups with complexes of the $L_nMX_2$ type containing phosphane (L=CO or tertiary phosphane, n=3 or 4, M=ruthenium or osmium, X=halogen and/or hydrogen) whereby all the groups of this type which are present are always hydrogenated.

Cationic ruthenium complexes which are suitable as homogeneous catalysts for the hydrogenation of olefines in acidic, methanolic solution, are described in J. C. S. Dalton 1973, pages 846 to 854. No hydrogenation of interior positioned double bonds takes place with these complexes.

The selective hydrogenation of polymeric unsaturated compounds which carry reducible groups containing nitrogen is particularly problematic since it is not possible to separate off by-products in this case or, at least, only with extremely great expenditure.

A method of hydrogenating CC-double bonds of diene-(meth)acrylonitrile copolymers with a large proportion of alternating diene nitrile units homogeneously with rhodium halogen complex catalysts in chlorobenzene is known from U.S. Pat. No. 3,700,637. The suitability of other metals such as platinum, ruthenium, iridium, palladium, rhenium, cobalt or copper, homogeneously or heterogeneously, is indicated.

In DE-OS No. 2 539 132 a selective hydrogenation of butadiene acrylonitrile copolymers which is dependent on a solvent, with the known rhodium catalyst is postulated, in which the CN-triple- and cis-double bonds are preserved and the vinyl and trans-double bonds are hydrogenated quantitatively if chlorobenzene is used as the solvent. In other solvents, in particular ketones, only low hydrogenation rates are achieved.

Finally, DE-OS No. 2 459 115 gives a method of homogeneously or, preferably, heterogeneously hydrogenating unsaturated polyhydroxy hydrocarbons with molecular weights of up to 4000 with the preservation of the hydroxyl groups with the aid of ruthenium catalysts. Aliphatic hydrocarbons, aromatic hydrocarbons, alcohols, ethers, esters and water are used as solvents for the heterogeneous hydrogenation process; no details are given of the homogeneous hydrogenation process. The polymers can apparently also contain, for example, acrylonitrile, as a comonomer, but no detailed descriptions are given, although it must be borne in mind that it is known from U.S. Pat. No. 3,454,644, example IX, that the nitrile group of benzonitrile is hydrogenated, in homogeneous Ru-catalysis in ethanol, to the amino group.

As the occurrence of rhodium is very small and rhodium is not only used in the chemical industry but primarily in the electrical industry, the glass industry and the ceramics industry and, most recently, especially in the motor car industry (exhaust catalysts), the possibility of a shortage of this precious metal in the future cannot be ruled out.

The object of the present invention was to provide a new homogeneous hydrogenation process, independent on rhodium, for the selective hydrogenation of unsaturated compounds which carry reducible groups containing nitrogen, which also makes it possible for polymeric unsaturated compounds which carry reducible groups containing nitrogen to be hydrogenated with the preservation of the reducible groups containing nitrogen.

The object was achieved, surprisingly, by the homogeneous reaction process with the use of special rutheniumhydrido phosphane complexes.

The invention provides, therefore, for the hydrogenation of unsaturated compounds which carry reducible groups containing nitrogen, in a homogeneous phase, with the preservation of the reducible groups containing nitrogen, characterised in that a compound of the formula $$RuH_{2n}L_{5-n}$$

is used as a catalyst, whereby
L signifies phosphane or arsane and
n signifies 1 or 2.

The phosphanes and arsanes preferably correspond to the formulas

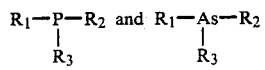

in which $R_1$, $R_2$ and $R_3$ can be the same or different and can signify alkyl, aryl, cycloalkyl and aralkyl.

Examples of alkyl residues are straight-chain or branched, saturated hydrocarbon residues with 1 to 20, preferably 1 to 12, in particular preferably 1 to 6 C-atoms.

Cycloalkyl residues are, for example, cyclic, saturated hydrocarbon residues with 5 to 7 C-atoms.

Aryl residues are, for example, aromatic hydrocarbon residues from the benzene series with 6 to 18, preferably 6 to 10 C-atoms.

Aralkyl residues are, for example, alkyl residues substituted by aryl, which consist of a striagth-chain or branched hydrocarbon residue with 1 to 6 C-atoms in the aliphatic part, and of a residue of the benzene series, preferably phenyl, in the aromatic part.

The alkyl-, cycloalkyl-, aryl-, and aralkyl residues described above can optionally be substituted by hydroxy, $C_1$- to $C_6$-alkoxy, $C_1$- to $C_6$-Carb-$C_1$-$C_4$-alkoxy, fluorine, chlorine or Di-$C_1$-$C_4$-alkyl amino groups and the cycloalkyl-, aryl- and aralkyl residues can also be substituted by $C_1$- to $C_6$-alkyl. Alkyl-, cycloalkyl- and aralkyl groups can contain keto groups.

As ligands L e.g. triphenyl phosphane, diethyl phenyl phosphane, tritolyl phosphane, trinaphthyl phosphane, diphenyl methyl phosphane, diphenyl butyl phosphane, tris-(p-carb methoxy phenyl)- phosphane, tris-(p-cyano phenyl)-phosphane, tributyl phosphane, tris-(trimethoxy phenyl) phosphanes, bis-(trimethyl phenyl)-phenyl phosphanes, bis-(trimethoxy phenyl)-phenyl phosphane, trimethyl phenyl-diphenyl phosphanes, trimethoxy phenyl diphenyl-phosphanes, tris-(dimethoxy phenyl)-phosphanes, bis-(dimethyl phenyl)-phenyl phosphanes, bis-(dimethoxy phenyl)-phenyl phosphanes, dimethyl phenyl diphenyl phosphanes, dimethoxy phenyl diphenyl phosphanes, diphenyl-trifluoro methyl phosphane, triphenyl arsane, ditolyl phenyl arsane, tris-(4-ethoxy phenyl)-arsane, diphenyl cyclo hexyl arsane, dibutyl phenyl arsane and diethyl phenyl arsane may be used.

Triaryl phosphanes, in particular triphenyl phosphane, are preferred.

Some of the complexes used are known. They can be prepared, for example, from ruthenium dichloride-tris-triphenyl phosphane by reduction (J. Organomet. Chem. 54, (1973) 259–264).

Nitriles, imines and oximes, for example, are used as unsaturated compounds which carry reducible groups containing nitrogen of which nitriles are preferred.

High-molecular, unsaturated compounds which carry reducible groups containing nitrogen are preferably copolymers containing nitrile groups of 85 to 50% by weight, preferably 82 to 55% by weight, at least of a conjugated diene, 15 to 50% by weight, preferably 18 to 45% by weight, at least of an unsaturated nitrile and 0 to 10% by weight, preferably 0 to 8% by weight, at least of another monomer which can be copolymerized with conjugated dienes and unsaturated nitriles.

For example, buta-1,3-diene, 2-methyl buta-1,3-diene, 2,3-dimethyl buta-1,3-diene and penta-1,3-diene are used as conjugated dienes, and acrylonitrile and methacrylonitrile are used as unsaturated nitriles.

Vinyl aromatic substances such as styrene, o-, m- or p-methyl styrene, ethyl styrene, vinyl naphthalene and vinyl pyridine, α, β-unsaturated mono carboxylic acids with 3 to 5 C-atoms such as acrylic acid, methacrylic acid and crotonic acid are used as other monomers, as well as α, β-unsaturated dicarboxylic acids with 4 to 5 C-atoms such as maleic, fumaric, citraconic and itaconic acid, as well as vinyl alkyl ether with 1 to 4 C-atoms in the alkyl portion.

Preferably, a binary copolymer made of butadiene and acrylonitrile is hydrogenated.

The molecular weight of the polymers is not critical and is between 500 and 500 000 g per mol, preferably between 1000 and 200 000 g per mol and, in particular, between 30 000 and 150 000 g per mol (number average, determined by gel permeation chromatography).

The conversions or the degrees of hydrogenation, resp., (percentage of hydrogenated CC-double bonds related to the total number of the CC-double bonds which were originally present in the polymer) can be up to 100%. The hydrogenation process can, however, be interrupted beforehand if necessary. Polymers with degrees of hydrogenation of over 80%, in particular of over 90%, preferably of over 95% are preferably prepared according to the process of the invention. The degree of hydrogenation is determined by means of IR- and NMR-spectroscopy.

In particular, low-molecular ketones with 3 to 10 C-atoms, in particular acetone, butanone, pentanones, cyclopentanone and cyclohexanone are used as solvents for the hydrogention process.

The concentration of the unsaturated compound, related to the total solution, is 1 to 90, preferably 5 to 40% by weight.

The concentration of catalyst, related to unsaturated compound (calculated as ruthenium), is 10 to 1000, preferably 10 to 600 ppm, more preferably 40 to 500 ppm.

The hydrogenation process is preferably carried out at 80° to 200° C., preferably at 100° to 180° C., in particular at 115° to 160° C. and 1 to 350 bar, preferably at 20 to 250 bar hydrogen pressure.

The catalyst can be separated off after the reaction by the usual methods and the product purified, for example, by distillation or crystallization.

In the case of a high-molecular compound the polymer is separated off from the solution using the usual methods, for example, by means of evaporation, by the injection of water vapour or by the addition of a non-solvent. A drying process follows for the removal of residual solvent or water.

The polymers hydrogenated according to the invention are hardened in the usual manner by means of a peroxide or sulphur vulcanization, provided that the vulcanization is not carried out by cross-linking by irridation.

Because of their excellent weather resistance, ozone resistance, oil resistance and hot air resistance, as well as resistance to a cold climate, these polymers can be used for high-grade rubber articles, such as seals, hoses, membranes, for cable insulations and cable coverings.

The low-molecular compounds hydrogenated according to the invention which carry reducible groups containing nitrogen, are valuable intermediate products for the preparation of active ingredients.

EXAMPLE 1

A solution of 220 g of statistical butadiene acrylonitrile copolymer with 34.9% by weight acrylonitrile, having a Mooney viscosity of ML 1+4 (100° C.) of 29 in 1800 ml butanone, which solution had been carefully purged with nitrogen, was placed in a 3-liter autoclave under nitrogen purging. Keeping the atmosphere inert a solution of 590 mg RuH$_4$(PPh$_3$)$_3$ in 200 ml butanone which had also been purged with nitrogen was added, and a pressure of 80 bar hydrogen was applied. The mixture was heated to 130° C. and then the reaction was continued at 140 bar hydrogen pressure for 4 hours at 130° C. The degree of hydrogenation of the polymer was determined using NMR- and IR-spectroscopy to be 95%.

EXAMPLE 2

According to the instructions in example 1, a hydrogenation process was carried out with 550 mg $RuH_2(PPh_3)_4$. The degree of hydrogenation of the polymer was 97% after 6 hours of reaction time.

We claim:

1. A process for the hydrogenation of the C=C double bonds of a polymer consisting essentially of
   (i) 85 to 50% by weight of copolymerized units of conjugated dienes selected from the group consisting of butadiene-1.3 and pentadiene-1.3,
   (ii) 15 to 50% by weight of copolymerized units of unsaturated nitriles selected from the group consisting of acrylonitrile and methacrylonitrile, and
   (iii) 0 to 10% by weight of copolymerized units of other copolymerizable monomer in a homogeneous phase up to a hydrogenation degree of more than 80% with preservation of the nitrile units, which process comprises reacting the polymer with hydrogen to a degree of hydrogenation greater than 80% at a pressure from 1 to 350 bar and a temperature from 80° to 200° C. in a ketone solvent having 3 to 10 carbon atoms in the presence of 10 to 1,000 ppm catalyst, based on polymer, which is a compound of the formula $$RuH_{2n}L_{5-n}$$

wherein L is of the formula $$R_1-P-R_2 \text{ or } R_1-As-R_2$$
   $$\phantom{R_1-P-}|\phantom{R_2 \text{ or } R_1-As-}|$$
   $$\phantom{R_1-P-}R_3\phantom{R_2 \text{ or } R_1-As-}R_3$$

wherein $R_1$, $R_2$ and $R_3$ are the same or different and each is alkyl having 1 to 20 carbon atoms, cycloalkyl having 5 to 7 carbon atoms, aryl having 6 to 18 carbon atoms or aralkyl having 1 to 6 alkyl carbon atoms, and n is the integer 1 or 2.

2. A process according to claim 1, characterised in that triaryl phosphanes are used as ligands L.

3. A process according to claim 1, characterised in that triphenyl phosphane is used as ligand L.

* * * * *